United States Patent
Grubbs et al.

(10) Patent No.: US 6,504,041 B2
(45) Date of Patent: Jan. 7, 2003

(54) SYNTHESIS OF RUTHENIUM OR OSMIUM METATHESIS CATALYSTS

(75) Inventors: Robert H. Grubbs, South Pasadena, CA (US); Tomas R. Belderrain, Seville (ES); Seth N. Brown, South Bend, IN (US); Thomas E. Wilhelm, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/967,198

(22) Filed: Sep. 28, 2001

(65) Prior Publication Data

US 2002/0022733 A1 Feb. 21, 2002

Related U.S. Application Data

(62) Division of application No. 09/672,585, filed on Sep. 28, 2000, now Pat. No. 6,313,332, which is a division of application No. 09/523,017, filed on Mar. 10, 2000, now Pat. No. 6,153,778, which is a division of application No. 09/253,042, filed on Feb. 19, 1999, now Pat. No. 6,048,993, which is a division of application No. 08/966,011, filed on Nov. 7, 1997, now Pat. No. 5,917,071.

(60) Provisional application No. 60/031,088, filed on Nov. 15, 1996.

(51) Int. Cl.$^7$ .............................. C07F 15/00; C07F 9/02; B01J 31/00

(52) U.S. Cl. ........................ 556/21; 556/23; 556/136; 502/152

(58) Field of Search .................... 556/21, 23, 136; 502/152

(56) References Cited

U.S. PATENT DOCUMENTS

| | | | | |
|---|---|---|---|---|
| 4,883,851 A | * | 11/1989 | Grubbs et al. | 526/170 |
| 4,945,135 A | * | 7/1990 | Grubbs et al. | 525/338 |
| 4,945,144 A | * | 7/1990 | Grubbs et al. | 525/338 |
| 5,198,511 A | * | 3/1993 | Brown-Wensley et al. | 526/113 |
| 5,296,566 A | * | 3/1994 | Brown-Wensley et al. | 526/171 |
| 5,312,940 A | * | 5/1994 | Grubbs et al. | 526/943 |
| 5,342,909 A | * | 8/1994 | Grubbs et al. | 526/170 |
| 5,554,778 A | * | 9/1996 | Beatty et al. | 556/136 |
| 5,689,003 A | * | 11/1997 | Beatty et al. | 556/136 |
| 5,710,298 A | * | 1/1998 | Grubbs et al. | 502/155 |
| 5,726,334 A | * | 3/1998 | Beatty et al. | 502/155 |
| 5,917,071 A | * | 6/1999 | Grubbs et al. | 502/152 |
| 6,313,332 B1 | * | 11/2001 | Grubbs et al. | 502/152 |

* cited by examiner

Primary Examiner—Porfirio Nazario-Gonzalez
(74) Attorney, Agent, or Firm—Pillsbury Winthrop LLP

(57) ABSTRACT

The present invention relates to the synthesis of highly active ruthenium and osmium carbene metathesis catalyst in good yield from readily available starting materials. The catalysts that may be synthesized are of the general formula

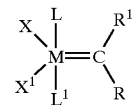

wherein:

M is ruthenium or osmium;

X and $X^1$ are independently any anionic ligand;

L and $L^1$ are any neutral electron donor ligand; and,

R and $R^1$ are each hydrogen or one of the following substituent groups: $C_2$–$C_{20}$ alkenyl, $C_2$–$C_{20}$ alkynyl, $C_1$–$C_{20}$ alkyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, the substituent group may be substituted with one or more groups selected from $C_1$–$C_5$ alkyl, halogen, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Specific synthetic protocols for vinyl alkylidene catalysts wherein R is hydrogen and $R^1$ is —$CHCR^{12}R^{13}$ and non-vinyl alkylidene catalysts are also disclosed. In addition to the ease of synthesis (typically a one-step synthesis), the reactions generally may be run at or above room temperature and the resulting products usually may be used without extensive post synthesis purification.

48 Claims, No Drawings

SYNTHESIS OF RUTHENIUM OR OSMIUM METATHESIS CATALYSTS

The present invention is a divisional of U.S. application Ser. No. 09/672,585 filed Sep. 28, 2000, now U.S. Pat. No. 6,313,332, which is a divisional of issued U.S. application Ser. No. 09/523,017 filed Mar. 10, 2000, now U.S. Pat. No. 6,153,778, which is a divisional of issued U.S. application Ser. No. 09/253,042 filed Feb. 19, 1999, now U.S. Pat. No. 6,048,993, which is a divisional of issued U.S. application Ser. No. 08/966,011 filed Nov. 7, 1997, now U.S. Pat. No. 5,917,071, all of which are entitled SYNTHESIS OF RUTHENIUM OR OSMIUM METATHESIS CATALYSTS by inventors Robert H. Grubbs, Tomas R. Belderrain, Seth N. Brown, Thomas E. Wilhelm, the contents of each of which are incorporated herein by reference.

This application claims the benefit of U.S. Provisional Application No. 60/031,088, filed Nov. 15, 1996 by inventors Robert H. Grubbs, Tomas Belderrain, and Seth N. Brown entitled "Synthesis of Ruthenium Metathesis Catalysts from Ruthenium Hydride Complexes" which is incorporated herein by reference.

The U.S. Government has certain rights in this invention pursuant to Grant No. CHE 9509745 awarded by the National Science Foundation.

BACKGROUND

The present invention relates to the synthesis of highly active ruthenium or osmium carbene metathesis catalysts. To the synthetic organic or polymer chemist, simple methods for forming carbon-carbon bonds are extremely important and valuable tools. One method of C—C bond formation that has proved particularly useful is transition-metal catalyzed olefin metathesis. The past two decades of intensive research effort has recently culminated in the discovery of well defined ruthenium and osmium carbene complex catalysts that are highly metathesis active and stable in the presence of a variety of functional groups.

These ruthenium and osmium carbene complexes have been described in U.S. Pat. Nos. 5,312,940 and 5,342,909 and U.S. patent applications Ser. Nos. 08/708,057, 08/282,827 and 08/693,789, all of which are incorporated herein by reference. The ruthenium and osmium carbene complexes disclosed in these patents and applications all possess metal centers that are formally in the +2 oxidation state, have an electron count of 16, and are penta-coordinated. These catalysts are of the general formula

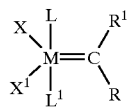

where M is ruthenium or osmium, X and $X^1$ are anionic ligands, and L and $L^1$ are neutral electron donors and R and R' are specific substituents that will be described in more detail below.

U.S. Pat. Nos. 5,312,940 and 5,342,909 disclose specific vinyl alkylidene ruthenium and osmium complexes in which the neutral electron donor ligands L and $L^1$ are triphenyl phosphines or diphenylmethyl phosphines. As disclosed in the patents, the catalysts are useful in catalyzing the ring opening metathesis polymerization ("ROMP") of strained olefins. U.S. patent applications Ser. Nos. 08/708,057 and 08/282,827 disclose specific vinyl alkylidene ruthenium and osmium complexes in which the neutral electron donor ligands L and $L^1$ are phosphines with at least one secondary-alkyl or cycloalkyl substituent. These secondary-alkyl phosphine catalysts are more metathesis active than the corresponding triphenyl phosphine catalysts and may be used to catalyze a variety of metathesis reactions involving acyclic and unstrained cyclic olefins. U.S. patent application Ser. No. 08/693,789 discloses specific non-vinyl alkylidene complexes that are more metathesis active than their vinyl alkylidene counterparts. The preferred catalyst disclosed in this application are benzylidene ruthenium and osmium carbene compounds.

As disclosed by U.S. Pat. Nos. 5,312,940 and 5,342,909, vinyl alkylidene catalysts may be synthesized by a variety of methods including the reaction of ruthenium or osmium compounds with cyclopropenes or phosphoranes, and neutral or anionic ligand exchange. Of these previous methods, the preferred method of making the catalysts is via the reaction of a substituted cyclopropene with a ruthenium or osmium dihalide. Unfortunately, this method is limited to the synthesis of vinyl alkylidene catalysts (i.e., catalysts in which R is hydrogen and $R^1$ is a substituted vinyl group) and cannot be used to directly synthesize the secondary-alkyl phosphine catalysts disclosed in the Ser. Nos. 08/282,826 and 08/282,827 applications. The synthesis of these secondary-alkyl phosphine catalysts further requires reacting the triphenyl phosphine catalysts produced from the cyclopropene reaction with secondary-alkyl phosphines in a ligand exchange reaction.

In part to overcome the fact that the cyclopropenes are not readily available and are generally limited to the synthesis of vinyl alkylidene catalysts, U.S. patent application Ser. No. 08/693,789 discloses a method for synthesizing alkylidene complex catalysts via the reaction of substituted diazoalkanes with ruthenium dihalides. The synthetic procedures disclosed in this application can be used to make non-vinyl alkylidene complex catalysts which are more metathesis active than their corresponding vinyl alkylidene counterparts. As in the cyclopropene based methods, the secondary-alkyl phosphine catalysts cannot be synthesized directly from the reaction of ruthenium dihalide and diazoalkanes. Instead, the secondary-alkyl phosphine catalysts must be synthesized by ligand exchange. Although the use of diazo starting materials greatly broadened the range of ruthenium and osmium carbene catalysts that could be synthesized, the danger of handling diazocompounds on a large scale severely restricts the commercial and laboratory utility of this method. In addition, the diazo method requires the synthesis to be conducted at low temperature (about −80° C. to −50° C.) and requires the use of considerable solvent in the final purification of the catalyst. As with the cyclopropene synthesis method, the secondary-alkyl phosphine catalysts must be synthesized using a multi-step ligand exchange procedure which may be time consuming and expensive and may result in lower product yields.

In both the cyclopropene and diazo synthesis methods the secondary-alkyl phosphine catalysts must be synthesized using a multi-step, ligand exchange procedure. Since the secondary-alkyl phosphine catalysts are more metathesis active than the triphenyl phosphine catalysts and therefore may have wider commercial utility, the necessity of a multi-step synthesis in these cases can be a severe limitation.

Although the previous methods have been adequate to make reasonable quantities of the ruthenium and osmium carbene catalysts, as the number of scientific and commercial applications of these catalysts continues to increase, a need exists for simple, safe, and inexpensive methods of synthesizing these compounds to fully exploit their potential.

SUMMARY

The present invention addresses this need and provides simple, safe, and less expensive methods of synthesizing ruthenium and osmium carbene catalysts. In general, one step syntheses are provided using stable, readily available starting materials. The processes result in good product yield without the need for expensive and sophisticated equipment. In addition, both vinyl and non-vinyl alkylidene catalysts may be synthesized. Moreover, the methods can produce catalysts in a form which makes post synthesis purification unnecessary.

In one aspect of the present invention, a method for synthesizing ruthenium and osmium carbene complex catalysts of the formula

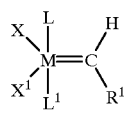

is provided where M is ruthenium or osmium; X and $X^1$ are any anionic ligand, preferably chloride; and L and $L^1$ are any neutral electron donor ligand, preferably tricycloalkylphosphines; and, $R^1$ may be any one of a variety of substituents which are described in detail below. In the preferred catalyst, $R^1$ is phenyl. In this embodiment of the invention, a compound of the formula

(n=1 or 2) is contacted with a compound of the formula $R^1C(X)(X^1)H$ in the presence of an olefin to yield the required ruthenium or osmium carbene complex catalyst.

In another aspect of the present invention, a method for synthesizing vinyl alkylidene catalysts of the formula

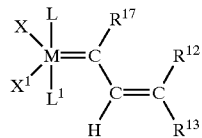

is provided where M, X, $X^1$, L, and $L^1$ are as described above and $R^{12}$, $R^{13}$, and $R^{17}$ may be the same or different and may be any one of a variety of substituents that are described in detail below. In the preferred catalyst, $R^{12}$ and $R^{13}$ are the same and are both methyls and $R^{17}$ is hydrogen. In this embodiment of the invention, a compound of the formula

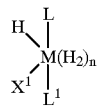

(n=1 or 2) is contacted with a compound of the formula

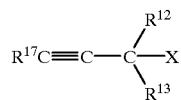

to yield the required ruthenium or osmium carbene complex catalyst.

Alternatively, the alkyne may be of the general formula, $R^{17}C \equiv CCR^{12}R^{13}R'$, wherein R' is hydroxyl. In this variation, the alkyne is reacted with the dihydrogen complex as above but then subsequently reacted with HX to form the above described vinyl alkylidene catalyst. However, in another variation of this reaction scheme, when R' is hydrogen or a $C_1-C_{20}$ alkyl, the method produces a non-vinyl alkylidene catalyst of the general formula, $(X)(X^1)(L)(L^1)M=C(R^{17})(CH_2CR^{12}R^{13}R')$.

In yet another aspect of the present invention, a method for synthesizing compounds of the formula

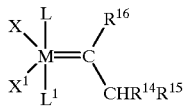

is provided where M, X, $X^1$, L, and $L^1$ are as described above and $R^{14}$, $R^{15}$, and $R^{16}$ may be any one of a variety of substituents that are described in detail below. In this embodiment of the invention, a compound of the formula

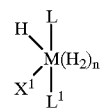

(n=1 or 2) is contacted with a compound of the formula

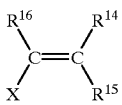

to yield the required ruthenium or osmium carbene complex catalyst.

DETAILED DESCRIPTION

General Description of the Catalysts

The methods of the present invention may be used to synthesize ruthenium or osmium carbene complex catalysts that include a ruthenium or osmium metal center that is in a +2 oxidation state, have an electron count of 16, and are penta-coordinated. More specifically, the methods of the present invention may be used to synthesize compounds with the formula

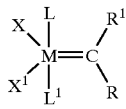

wherein
 M is ruthenium or osmium;
 X and $X^1$ are independently any anionic ligand;

L and L¹ are any neutral electron donor ligand;

R and R¹ are each hydrogen or one of the following substituent groups: $C_1$–$C_{20}$, alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the R¹ substituent may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In a preferred embodiment, the R substitutent is hydrogen and the R¹ substituent is one of the following: (1) hydrogen; (2) $C_1$–$C_{20}$ alkyl; (3) $C_2$–$C_{20}$ alkenyl (4) aryl; (5) $C_1$–$C_{20}$ alkyl substituted with one or more groups selected from the group consisting of aryl, halogen, hydroxy, $C_1$–$C_{20}$ alkoxy, and $C_2$–$C_5$ alkoxycarbonyl; and (6) aryl substituted with one or more groups selected from the group consisting of $C_1$–$C_5$ alkyl, aryl, hydroxyl, $C_1$–$C_5$ alkoxy, amino, nitro, and halogen. In a more preferred embodiment, the R¹ substituent is phenyl or phenyl substituted with a group selected from the group consisting of chloride, bromide, iodide, fluoride, —$NO_2$, —$NMe_2$, methoxy, and methyl. In the most preferred embodiment, the R¹ substituent is phenyl.

The L and L¹ ligands may be the same or different and may be any neutral electron donor ligand. In a preferred embodiment, the L and L¹ ligands may be the same or different and may be phosphines, sulfonated phosphines, phosphites, phosphinites, phosphonites, arsines, stibines, ethers, amines, amides, imines, sulfoxides, carboxyls, nitrosyls, pyridines, and thioethers. In a more preferred embodiment, the L and L¹ ligands may be the same or different and are phosphines of the formula $PR^3R^4R^5$, where $R^3$ is a secondary alkyl or cycloalkyl group, and $R^4$ and $R^5$ are the same or different and may be aryl, $C_1$–$C_{10}$ primary alkyl, secondary alkyl, or cycloalkyl groups. In the most preferred embodiment, the L and L¹ ligands may be the same or different and are —P(cyclohexyl)$_3$, —P(cyclopentyl)$_3$, or —P(isopropyl)$_3$.

The X and X¹ ligands may be the same or different and may be any anionic ligand. In a preferred embodiment, the X and X¹ ligands may be the same or different and may be a halogen, hydrogen or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Each group may optionally be substituted with $C_1$–$C_5$ alkyl, halogen, $C_1$–$C_5$ alkoxy or with a phenyl group. The phenyl group in turn may optionally be substituted with halogen, $C_1$–$C_5$ alkyl or $C_1$–$C_5$ alkoxy. In a more preferred embodiment, the X and X¹ ligands may be the same or different and may be chloride, bromide, iodide, hydrogen or a moiety selected from a group consisting of: benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. Each moiety may optionally be substituted with $C_1$–$C_5$ alkyl or a phenyl group. The phenyl group may optionally be substituted with halogen, $C_1$–$C_5$ alkyl or $C_1$–$C_5$ alkoxy. In an even more preferred embodiment, the X and X¹ ligands may be the same or different and may be chloride, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiment, X and X¹ are both chloride.

The most preferred catalysts are

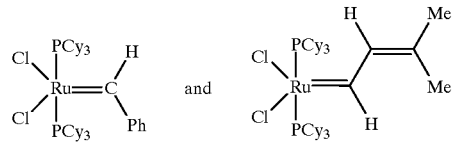

where Cy is cyclohexyl or cyclopentyl and Me is methyl.

The above catalysts are stable in the presence of a variety of functional groups including hydroxyl, thiol, ketone, aldehyde, ester, ether, amine, imine, amide, nitro, carboxylic acid, disulfide, carbonate, isocyanate, carbodiimide, carboalkoxy, and halogen. Therefore, the starting materials and products of the reactions described below may contain one or more of these functional groups without poisoning the catalyst. In addition, the catalysts are stable in the presence of aqueous, organic, or protic solvents, for example, aromatic hydrocarbons, chlorinated hydrocarbons, ethers, aliphatic hydrocarbons, alcohols, water, or mixtures of the above. Therefore, the reactions described below may be carried out in one or more of these solvents without poisoning the catalyst product.

General Synthetic Schemes

The present invention relates to new routes for synthesizing the above-described ruthenium and osmium carbene catalysts which eliminate many of the problems associated with previous methods. Unless explicitly stated otherwise, the substituents of the catalyst are as defined above.

We have discovered that the ruthenium and osmium carbene catalysts may be synthesized in one-step syntheses using readily available and stable carbene and metal sources. As will be described in detail below, the methods of the present invention allow for the synthesis of ruthenium and osmium carbene complex compounds without the use of unstable starting materials and using reactions that may be run at room temperature or above. The method also allows for the preparation of catalysts with varying anionic and neutral electron donor ligands and varying substituents on the carbene carbon. The methods of the present invention generally yield the carbene complexes in greater than 90% yield and are sufficiently clean that the resulting catalysts may be used without extensive post synthesis purification. As discussed in the background section, all of these aspects of the present invention possess important advantages over the existing methods.

We have discovered three routes through which the catalysts may be synthesized involving a ruthenium or osmium dihydrogen complex and a simple organic compound. The two general forms of the dihydrogen complex are $M(H)_2(H_2)_nL^1L$ and $M(H)X(H_2)_nL^1L$ wherein M, X, L and L¹ are as previously defined and n is 1 or 2. Because the dissociation of the first dihydrogen species is facile, the single dihydrogen (n=1) and bis(dihydrogen) (n=2) complexes are essentially interchangeable. In general, the bis(dihydrogen) complex predominates in the solid form of the complex and the single(dihydrogen) complex predominates in solution.

In the first route, the dihydrogen complex is $M(H)_2(H_2)_nL^1L$ and the organic compound is a substituted alkane which includes a carbon atom bearing the X, X¹, and R¹ substituents of the catalyst. In the second route, the dihydrogen complex is $M(H)(X)(H_2)_nL^1L$ and the organic compound is a substituted alkyne. In the third route, the dihydrogen complex is $M(H)(X)(H_2)_nL^1L$ and the organic compound is an alkene (olefin).

For clarity and ease of presentation, specific reaction conditions and procedures are collected together in the final Experimental Procedures section.

The Alkane Route

This embodiment of the invention may be summarized in Reaction Scheme 1, below.

REACTION SCHEME 1

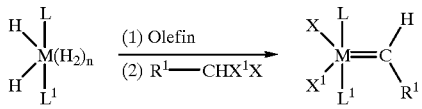

This embodiment includes a process for synthesizing a compound of the formula

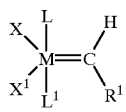

which comprises the step of contacting a compound of the formula

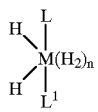

with a compound of the formula $R^1C(X)(X^1)H$ in the presence of an olefin. M, $R^1$, X, $X^1$, L, and $L^1$ are as described defined in the catalysts section and n is either 1 or 2.

In preferred embodiments of the alkane method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C_1$–$C_{10}$ primary alkyl, secondary alkyl, or cycloalkyl groups; X and $X^1$ ligands are each a halogen, benzoate, $C_1$–$C_5$ carboxylate, $C_1$–$C_5$ alkyl, $C_1$–$C_5$ alkoxy, $C_1$–$C_5$ alkylthio, aryl, or $C_1$–$C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2Co$, PhO, MeO, EtO, tosylate, mesylate, and trifluoromethanesulfonate; $R^1$ is hydrogen or a substituted or unsubstituted $C_1$–$C_{20}$ alkyl or aryl wherein the substituted group is selected from a group consisting of aryl, halogen, hydroxy, amino, nitro, $C_1$–$C_5$ alkyl, $C_1$–$C_5$ alkoxy, and $C_2$–$C_5$ alkoxycarbonyl; and the olefin is one which does not readily undergo metathesis reactions or regenerate the same species upon metathesis.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^1$ substituent is an substituted or an unsubstituted aromatic hydrocarbon wherein the substituted group is selected from the group consisting of chloride, bromide, iodide, fluoride, —NO$_2$, —NMe$_2$, methoxy, and methyl; and the olefin is cyclohexene or styrene.

In the most preferred embodiments: L and $L^1$ ligands are each either —P(cyclohexyl)$_3$ or —P(cyclopentyl)$_3$; X and $X^1$ ligands are each chloride; $R^1$ substituent is a substituted or unsubstituted phenyl wherein the substituted group is selected from the group consisting of chloride, bromide, iodide, fluoride, —NO$_2$, —NMe$_2$, methoxy, and methyl; and the olefin is cyclohexene.

As stated previously, it is preferred that the olefin selected for use in this synthetic route is one which does not readily undergo metathesis. When a metathesis active olefin such as ethylene is used, the expected product may not be generated in high yields due to a potential metathesis reaction between the olefin and the product catalyst. For example, when $Ru(H)_2(H_2)_2(PCy_3)_2$ was reacted with either PhCHCl$_2$ or Cl$_2$CHCO$_2$Me in the presence of ethylene, instead of the expected benzylidene and ester carbene, a methylidene complex was formed. Observations of the carbene proton resonances of the intermediates ($\delta$=20.59 and 20.15 respectively) as well as the formation of styrene and methyl methacrylate confirm that this is due to the subsequent metathesis reaction of ethylene with the resulting benzylidene and ester carbene.

However, this subsequent metathesis reaction is substantially eliminated when a less active olefin is used such as cyclohexene. For example, when $Ru(H)_2(H_2)_2(PCy_3)_2$ was reacted with PhCHCl$_2$, Cl$_2$CHCO$_2$Me or CH$_2$Cl$_2$ in the presence of cyclohexene, the corresponding carbenes were formed in good yield. When these reactions were monitored by $^{31}$P NMR using triphenylphosphine oxide as the internal standard, the NMR experiments showed that these conversions were essentially quantitative.

Alkyne Route

One version of this embodiment of the invention may be summarized in Reaction Scheme 2, below.

REACTION SCHEME 2

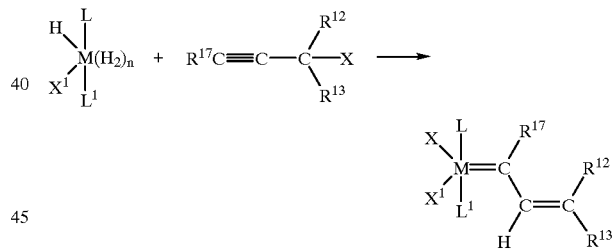

This embodiment includes a process for synthesizing a compound of the formula

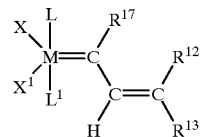

which comprises the step of contacting a compound of the formula

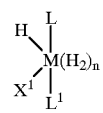

with a compound of the formula

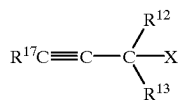

wherein M, X, $X^1$, L, and $L^1$ are as previously defined in the catalysts section.

Alternatively, the alkyne may be of the general formula, $R^{17}C\equiv CCR^{12}R^{13}R'$, wherein R' is hydroxyl. In this variation, the alkyne is reacted with the dihydrogen complex as above but then subsequently reacted with HX to form the above described catalyst. However, in another variation of this reaction scheme, when R' is hydrogen or a $C_1$–$C_{20}$ alkyl, the method produces a catalyst of the general formula, $(X)(X^1)(L)(L^1)M=C(R^{17})(CH_2CR^{12}R^{13}R')$.

In either version, the remaining variables are n which is either 1 or 2; $R^{17}$ which is hydrogen, aryl or $C_1$–$C_{18}$ alkyl; and $R^{12}$ and $R^{13}$ which are each hydrogen or one of the following substituent groups: $C_1$–$C_{18}$ alkyl, $C_2$–$C_{18}$ alkenyl, $C_2$–$C_{18}$ alkynyl, aryl, $C_1$–$C_{18}$ carboxylate, $C_1$–$C_{18}$ alkoxy, $C_2$–$C_{18}$ alkenyloxy, $C_2$–$C_{18}$ alkynyloxy, aryloxy, $C_2$–$C_{18}$ alkoxycarbonyl, $C_1$–$C_{18}$ alkylthio, $C_1$–$C_{18}$ alkylsulfonyl and $C_1$–$C_{18}$ alkylsulfinyl; wherein the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the $R^{12}$ and $R^{13}$ substituent groups may further include one or more functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of the alkyne method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C_1$–$C_{10}$ primary alkyl, secondary alkyl, or cycloalkyl groups; X and $X^1$ ligands are each a halogen, benzoate, $C_1$–$C_5$ carboxylate, $C_1$–$C_5$ alkyl, $C_1$–$C_5$ alkoxy, $C_1$–$C_5$ alkylthio, aryl, or $C_1$–$C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; $R^{12}$ and $R^{13}$ are each substituted or unsubstituted $C_1$–$C_{18}$ alkyl or aryl wherein the substituted group is selected from a group consisting of aryl, halogen, hydroxy, amino, nitro, $C_1$–$C_5$ alkyl, $C_1$–$C_5$ alkoxy, and $C_2$–$C_5$ alkoxycarbonyl; and $R^{17}$ is hydrogen or methyl.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^{12}$ and $R^{13}$ are each substituted or unsubstituted aromatic hydrocarbon wherein the substituted group is selected from the group consisting of chloride, bromide, iodide, fluoride, —NO$_2$, —NMe$_2$, methoxy, and methyl; and $R^{17}$ is hydrogen.

In the most preferred embodiments: L and $L^1$ ligands are each either —P(cyclohexyl)$_3$ or —P(cyclopentyl)$_3$; X and $X^1$ ligands are each chloride; $R^{12}$ and $R^{13}$ are each substituted or unsubstituted phenyl or wherein the substituted group is selected from the group consisting of chloride, bromide, iodide, fluoride, —NO$_2$, —NMe$_2$, methoxy, and methyl; and $R^{17}$ is hydrogen.

This embodiment of the invention is an extremely efficient method for synthesizing the above described ruthenium and osmium vinyl alkylidene catalysts in essentially a one pot synthesis. Because the metal complex need not be isolated, it may be generated in situ and then subsequently reacted with a substituted alkyne to form the desired product.

In addition to the ease of synthesis, the embodiment also results in high product yields. For example, the hydrido chloride complex Ru(H)(Cl)(H$_2$)(PCy$_3$)$_2$ reacts rapidly with commercially available 3-chloro-3-methyl-1-butyne in methylene chloride to form the carbene complex Ru(Cl)$_2$(PCy$_3$)$_2$(=CH—CH=Me$_2$) in 95.2% isolated yield. When this reaction was monitored by $^1$H NMR, it was found that the reaction is completed in less than ten minutes, even at −30° C. At this temperature, integration against an internal standard reveals that the yield is approximately 99.5%.

Reactions with other alkynes, especially propargylic halides, were found to react similarly. Ruthenium carbenes Ru(Cl$_2$)(PCy$_3$)$_2$(=CH—CH=(CH$_2$)$_5$) and Ru(Cl$_2$)(PCy$_3$)$_2$(=CH—CH=CHPh) were formed from the corresponding alkynes in essentially quantitative yields, although a trace of the ruthenium (IV) complex, Ru(H)$_2$(Cl)$_2$(PCy$_3$)$_2$ was formed as a byproduct. Interestingly, the amount of the byproduct increased as the steric bulk of the alkyne decreased. For example, the monomethyl substituted HC≡CCH(CH$_3$)Cl formed the carbene product Ru(Cl)$_2$(PCy$_3$)$_2$(=CH—CH=Me) and the byproduct Ru(H)$_2$(Cl)$_2$(PCy$_3$)$_2$ in an 8:1 ratio, and HC≡CCH2Cl formed the carbene product Ru(Cl)$_2$(PCy$_3$)$_2$(=CH—CH=CH$_2$) and the byproduct in a 0.8:1 ratio.

Changing X also affected the amount of the byproduct formed. For example, the dimethyl-substituted propargyl bromide, HC≡CC(Me)$_2$Br gives 30:1 of the expected mixed halogen carbene RuClBr(PCy$_3$)$_2$(=CH—CH=CMe$_2$) to the mixed halogen Ru(IV) species RuClBr(H)$_2$(PCy$_3$)$_2$ which is substantially different than from the greater than 200:1 ratio seen with the corresponding chloride, HC≡CC(Me)$_2$Cl. As a result, tertiary propargylic halide, especially tertiary propargylic chlorides are most preferred.

Moreover, ratio of carbene to Ru(IV) byproduct can be improved dramatically if the solvent is changed from dichloromethane to benzene or toluene. By switching solvents, the 8:1 and 0.8:1 product to byproduct ratios of HC≡CCH(CH$_3$)Cl and HC≡CCH$_2$Cl were improved to 30:1 and 37:1 respectively.

When L and $L^1$ groups are triaryl phosphines, Reaction Scheme 2 may be modified by replacing a dihydrogen species in the starting complex with a third phosphine ligand. The resulting hydrido complex will be of the form M(H)(Cl)(H$_2$)LL$^1$L$^2$ or M(H)(Cl)LL$^1$L$^2$ depending on the starting dihydrogen species. In all other respects, M, X, $X^1$, $R^{12}$, $R^{13}$, and $R^{17}$ are as described above. Reaction Scheme 2A shows one version of this embodiment.

REACTION SCHEME 2A

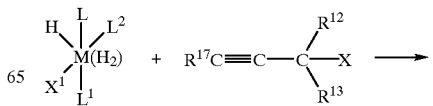

-continued

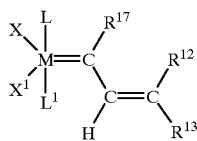

Alkene Route

This embodiment of the invention may be summarized in Reaction Scheme 3, below.

REACTION SCHEME 3

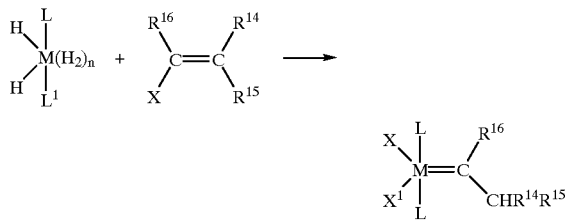

This embodiment includes a process for synthesizing a compound of the formula

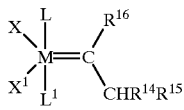

This process comprises the step of contacting a compound of the formula

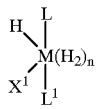

with a compound of the formula

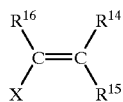

M, X, $X^1$, L, and $L^1$ are as described defined in the catalysts section; n is either 1 or 2; and $R^{14}$, $R^{15}$, and $R^{16}$ are each is hydrogen or one of the following substituent groups: $C_1$–$C_{19}$ alkyl, $C_2$–$C_{19}$ alkenyl, $C_2$–$C_{19}$ alkynyl, aryl, $C_1$–$C_{19}$ carboxylate, $C_1$–$C_{19}$ alkoxy, $C_2$–$C_{19}$ alkenyloxy, $C_2$–$C_{19}$ alkynyloxy, aryloxy, $C_2$–$C_{19}$ alkoxycarbonyl, $C_1$–$C_{19}$ alkylthio, $C_1$–$C_{19}$ alkylsulfonyl and $C_1$–$C_{19}$ alkylsulfinyl; wherein the substituent group may be substituted with one or more groups selected from $C_1$–$C_5$ alkyl, $C_1$–$C_5$ alkoxy, and aryl. When the substitute aryl group is phenyl, it may be further substituted with one or more groups selected from a halogen, a $C_1$–$C_5$ alkyl, or a $C_1$–$C_5$ alkoxy. Moreover, the $R^{14}$, $R^{15}$, and $R^{16}$ substituent groups may further include one or more functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of the alkene method: M is ruthenium; L and $L^1$ ligands are each a phosphine of the formula $PR^3R^4R^5$, where $R^3$ is a secondary alkyl or cycloalkyl group, and $R^4$ and $R^5$ are each aryl, $C_1$–$C_{10}$ primary alkyl, secondary alkyl, or cycloalkyl groups; X and $X^1$ ligands are each a halogen, benzoate, $C_1$–$C_5$ carboxylate, $C_1$–$C_5$ alkyl, $C_1$–$C_5$ alkoxy, $C_1$–$C_5$ alkylthio, aryl, or $C_1$–$C_5$ alkyl sulfonate including chloride, bromide, iodide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; $R^{14}$ and $R^{15}$ are each substituted or unsubstituted $C_1$–$C_{18}$ alkyl or aryl wherein the substituted group is selected from a group consisting of aryl, halogen, hydroxy, amino, nitro, $C_1$–$C_5$ alkyl, $C_1$–$C_5$ alkoxy, and $C_2$–$C_5$ alkoxycarbonyl; and $R^{16}$ is hydrogen.

In especially preferred embodiments: L and $L^1$ ligands are each —P(cyclohexyl)$_3$, —P(cyclopentyl)$_3$, or —P(isopropyl)$_3$; X and $X^1$ ligands are each a halogen; $R^{14}$ and $R^{15}$ are each substituted or unsubstituted aromatic hydrocarbon wherein the substituted group is selected from the group consisting of chloride, bromide, iodide, fluoride, —$NO_2$, —$NMe_2$, methoxy, and methyl; and $R^{16}$ is hydrogen.

In the most preferred embodiments: L and $L^1$ ligands are each either —P(cyclohexyl)$_3$ or —P(cyclopentyl)$_3$; X and $X^1$ ligands are each chloride; $R^{14}$ and $R^{15}$ are each substituted or unsubstituted phenyl or wherein the substituted group is selected from the group consisting of chloride, bromide, iodide, fluoride, —$NO_2$, —$NMe_2$, methoxy, and methyl; and $R^{16}$ is hydrogen.

When L and $L^1$ groups are triaryl phosphines, Reaction Scheme 3 may be modified by replacing a dihydrogen species in the starting complex with a third phosphine ligand. The resulting hydrido complex will be of the form $M(H)(Cl)(H_2)LL^1L^2$ or $M(H)(Cl)LL^1L^2$ depending on the starting dihydrogen species. In all other respects, M, X, $X^1$, $R^{14}$, $R^{15}$, and $R^{16}$ are as described above. Reaction Scheme 3A shows one version of this embodiment.

REACTION SCHEME 3A

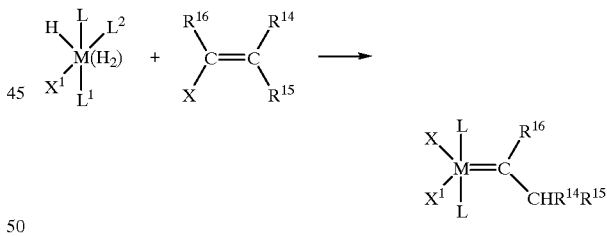

Because the alkene route reactions appears to be less efficient than the other two methods, the alkane route is generally the preferred method when non-vinyl alkylidene catalyst are to be synthesized. For example, $Ru(H)(Cl)(H_2)(PCy_3)_2$ reacts with vinyl chloride to give the expected carbene $Ru(Cl)_2(PCy_3)_2(=CHCH_3)$, the methylidene complex $Ru(Cl)_2(PCy_3)_2(=CH_2)$, and the ruthenium (IV) byproduct $Ru(H)_2(Cl)_2(PCy_3)_2$. The methylidene complex is a result of a subsequent cross metathesis reaction between the intended carbene product and vinyl chloride (which also results in the formation of 1-chloropropene). However, even when the total carbene products are taken into account, the ratio of carbene to Ru(IV) byproduct is a modest 2.1:1. Unlike the alkyne route, increasing the steric bulk at the alkene's β-carbon (to suppress β-addition), did not improve the carbene yield.

Alternative Synthesis for Ru(X)$_2$(L)$_2$(=CHR$^1$):

In this method, Ru(1,5-cyclooctadiene)(cyclooctatriene) (hereinafter referred to as "Ru(COD)(COT)") is used instead of the dihydrogen complex to synthesize catalysts of the general formula Ru(X)$_2$(L)$_2$(=CHR$^1$) wherein:

R$^1$ is as previously defined in the catalyst section;

X is a halogen; and,

L is a phosphine of the formula PR$^3$R$^4$R$^5$, where R$^3$ is a secondary alkyl or cycloalkyl group, and R$^4$ and R$^5$ are independently selected from aryl, C$_1$–C$_{10}$ primary alkyl, secondary alkyl, or cycloalkyl groups. In preferred embodiments, X is chloride and L is P(cyclohexyl)$_3$, P(cyclopentyl)$_3$, or P(isopropyl)$_3$. R$^1$CHX$_2$ is added to a solution of Ru(COD)(COT) in the presence of phosphine, L, in a suitable solvent at room temperature to generate the product, Ru(X)$_2$(L)$_2$(=CHR$^1$). Illustrative examples of suitable solvents include but are not limited to toluene, benzene and dichloromethane.

The general mechanism of reaction involves two steps: the oxidative addition of the alkyl dihalide to the Ru(0) species followed by an α-halide elimination. An illustrative example of this method is shown in Reaction Scheme 4 which results in a 50% product yield of RuCl$_2$(PCy$_3$)$_2$(=CHPh).

REACTION SCHEME 4

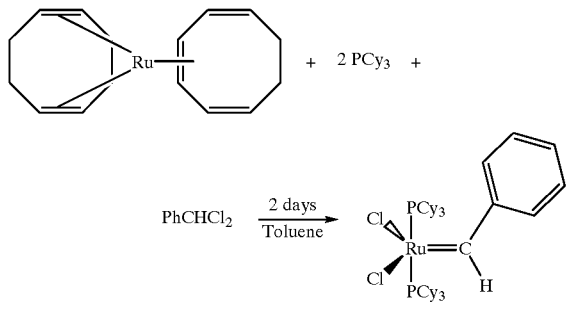

However, this synthetic route presents two potential limitations. The first is that although good yields have been reported, Ru(COD)(COT) is difficult and tedious to synthesize. The second is that the formation of phosphonium salts, such as PCy$_3$CHClR$^{1+}$Cl$^-$ when X=Cl and L=PCy$_3$, may potentially limit the viability of this route for some carbene catalysts. For example, while RuCl$_2$(PCy$_3$)$_2$(=CHPh) and RuCl$_2$(PCy$_3$)$_2$(=CH$_2$) may be synthesized in this manner, RuCl$_2$(PCy$_3$)$_2$(=CHCO$_2$Me) cannot be synthesized using Cl$_2$CHCO$_2$Me because of the formation of the phosphonium salt, [Cy$_3$PCHClCHCO$_2$Me]$^+$Cl$^-$ as a side reaction.

Alternative Synthesis for RuCl2(PCy3)2(=CHPh):

This alternative route is a variation of the alkane route that was previously described and takes advantage of a potential metathesis reaction between the olefin used in the reaction and the carbene product. First, RuCl$_2$(PCy$_3$)$_2$(=CHCO$_2$Me) is formed by reaction Ru(H)$_2$(H$_2$)$_2$(PCy$_3$) with Cl$_2$CHCO$_2$Me in the presence of the olefin, styrene, in an application of the above described alkane reaction. The formed carbene RuCl$_2$(PCy$_3$)$_2$(PCy$_3$)(=CHCO$_2$Me) undergoes a subsequent metathesis reaction with styrene to produce the final product RuCl$_2$(PCy$_3$)$_2$(=CHPh).

Experimental Procedures

Synthesis of Ru(H)$_2$(H$_2$)$_2$(PCy$_3$)$_2$.

In general, unless explicitly noted otherwise, all solvents used are degassed prior to use. [RuCl$_2$(COD)]$_x$ (6.0 g, 21.43 mmol), PCy$_3$ (12.0 g, 42.86 mmol), and NaOH (7.2 g) were placed in a 500 mL Fisher-Porter bottle. [RuCl$_2$(COD)]$_x$ is a polymeric complex produced from the reaction of RuCl$_3$ with COD. Degassed sec-butyl alcohol (250 mL) was added, and the suspension was pressurized under H$_2$ (2 atm) and heated at 90° C. The system was repressurized several times, an indication of H$_2$ uptake. The reaction mixture was stirred overnight. The system was allowed to cool to room temperature under H$_2$ pressure. A pale yellow crystalline precipitate was obtained. All of the following manipulations were carried out under H$_2$ pressure. Water (30 mL) was added to the resulting mixture, and the mixture was filtered though a glass frit filter. The filtrate was washed twice with water (30 mL portions) and with methanol (twice with 20 mL portions. The solid was dried under a H$_2$ stream. 11.8 g (83% yield) of a pale yellow crystalline compound was obtained. The NMR spectra of this product were identical to those previously reported in the literature for Ru(H)$_2$(H$_2$)$_2$(PCy$_3$)$_2$.

Synthesis of RuCl$_2$(PCy$_3$)$_2$(=CHPh).

To a suspension of Ru(H)$_2$(H$_2$)$_2$(PCy$_3$)$_2$ (1.0 g, 1.50 mmol) in pentane (40 mL), cyclohexene (1.5 mL, 14.80 mmol) was added. After 2 minutes, a yellow solution is obtained, and after 15 minutes, a pale yellow precipitate is formed. The reaction mixture was stirred for 1 hour. The volatiles were removed under vacuum. Pentane was added to the solid. Addition of PhCHCl$_2$ (0.4 mL, 3.11 mmol) led to the formation of a red solution, which was stirred for 45 minutes. The solvent was evaporated, and the residue was washed with cold methanol (three times with 10 mL portions). 0.75 g (61% yield) of a purple solid was obtained whose NMR spectra were identical to the compound RuCl$_2$(PCy$_3$)$_2$(=CHPh).

Synthesis of RuCl$_2$(PCy$_3$)$_2$(=CH$_2$) and RuCl$_2$(PCy$_3$)$_2$(=CHCO$_2$Me).

RuCl$_2$(PCy$_3$)$_2$(=CH$_2$) and RuCl$_2$(PCy$_3$)$_2$(=CHCO$_2$Me) were prepared in an analogous manner as above except that Cl$_2$CH$_2$ and Cl$_2$CHCO$_2$Me were added as the dihalo compounds respectively. In the case of the synthesis of RuCl$_2$(PCy$_3$)$_2$(=CH$_2$), because the reaction is slower as monitored by NMR, the reaction mixture was stirred overnight after the addition of Cl$_2$CH$_2$.

Selective spectroscopic data for RuCl$_2$(PCy$_3$)$_2$(=CHCO$_2$Me): $^1$H NMR (300 MHz, C$_6$D$_6$): δ 20.15 (s, Ru=CH), 3.53 (s, CO2CH3); $^{13}$C NMR (125.71, CD$_2$Cl$_2$, –30° C.) δ 276.37 (t, J(P,C)=5.1 Hz, Ru=CH), 178.69 (s, CO$_2$Me), 50.84 (s, CO$_2$CH$_3$); $^{31}$P (161.9 MHz, C$_6$D$_6$) δ 38.66 (s, PCy$_3$); IR (Nujol) ν 1721 cm$^{-1}$ (C=O—(ester)).

Ru(H)$_2$(H$_2$)$_2$(PCy$_3$)$_2$+styrene +α,α-dichlorotoluene.

Styrene (0.2 mL, 1.7 mmol) was added to a solution of Ru(H)$_2$(H$_2$)$_2$(PCy$_3$)$_2$ (0.54 g; 0.77 mmol) in toluene (20 mL). After 15 min, α,α-dichlorotoluene (0.1 mL) was added to the resulting deep red solution. The reaction mixture was stirred for 45 min. The solvent was removed and the residue washed with methanol and acetone affording the isolation of a purple solid, identified as Ru(=CHPh)Cl$_2$(PCy$_3$)$_2$ by NMR. Yield 25%.

Isolation and utility of an alkane-reaction intermediate where the olefin is cyclohexene: Ru(cyclohexene)$_2$(H$_2$)(PCy$_3$)$_2$.

Cyclohexene (5 mL was added to Ru(H$_2$)(H$_2$)$_2$(PCy$_3$)$_2$$^{13}$ (1.1 g; 1.65 mmol). The formation of a red solution was observed and immediately a pale yellow solid precipitated out. Pentane was added (20 mL) and the suspension was stirred for 2 h. The solid was isolated by filtration. Yield: 81%. $_1$H in C$_6$D$_6$: –5. (br s, 2H, H$_2$), 1.2–2.0 (m, 66H, PCy$_3$), 3.0 (s, 1H, CH$_{olefin}$), 20.1 ppm; $^{31}$P{$^1$H} 59 ppm (s).

Addition of $R^1CHX^1X$ to this intermediate, $Ru(cyclohexene)_2(H_2)(PCy_3)_2$ results in the ruthenium catalyst, $RuX^1X(PCy_3)_2(R^1)$. As a result, the specific intermediate, $Ru(cyclohexene)_2(H_2)(PCy_3)_2$, or any intermediate of the general form, $Ru(olefin)_2(H_2)(PCy_3)_2$, may replace $Ru(H)_2(H_2)_2(PCy_3)_2$ and the olefin in the alkane reaction route.

For example, $Ru(=CHPh)Cl_2(PCy_3)_2$ was synthesized by adding α,α-dichlorotoluene (5 μL) to a solution of $Ru(cyclohexene)_2(H_2)(Cy_3P)_2$ (20 mg; 2.68·10−2 mmol) in $C_6D_6$ (0.5 mL) The solution turned deep red and the $^1H$ and $^{31}P\{^1H\}$ NMR spectra showed the quantitative conversion to $Ru(=CHPh)Cl_2(PCy_3)_2$. Similarly, $Ru(=CHCOOMe)Cl_2(PCy_3)_2$ was synthesized by adding methyl dichloroacetate (5 μL) to a solution of $Ru(cyclohexene)_2(H_2)(PCy_3)_2$ (20 mg; 2.68·10−2 mmol) in $C_6D_6$ (0.5 mL). The solution turned violet and the $^1H$ and $^{31}P$ NMR spectra showed the quantitative conversion to $Ru(=CHCOOMe) Cl_2 (PCy_3)_2$. $^1H$ in $C_6D_6$: 1.2–2.7 (m, 66H, $PCy_3$), 3.5 (s, 3H, $COOCH_3$), 20.1 ppm (s, CH carbene unit); $^{31}P\{^1H\}$ in $C_6D_6$ 38 ppm (s, $PCy_3$).

Synthesis of $Ru(H)(Cl)(H_2)_2(PCy_3)_2$.

$[RuCl_2(COD)]_x$ (4.00 g, 14.28 mmol) and tricyclohexylphosphine (8.46 g of 97% from Strem, 29.26 mmol) were placed in a 500 ml, high pressure system equipped with a pressure gauge. To this system, 200 mL of degassed sec-butanol and triethylamine (1.99 mL, 14.28 mmol) were added. The system is then placed under vacuum, and purged with hydrogen. After purging, the system is pressurized with 1.5 atm of hydrogen, sealed, and heated to 80° C. for a total of 20 hours. When the pressure dropped below an atmosphere the system was cooled and re-pressurized, approximately every 20–30 minutes for the first several hours.

Generation of Ru(H) (Cl) $(H_2)_2(PCy_3)_2$ can also be accomplished in a suitably sized, thick walled teflon-valved Strauss flask. Depending on the scale of the reaction and the size of the flask, the system is re-pressurized with hydrogen gas after several hours. Alternatively, the reaction can be carried out by bubbling $H_2$ gas at atmospheric pressure.

Isolation of the air-sensitive orange solid was accomplished by allowing the system to cool to room temperature and adding a volume (200 mL) of degassed methanol to insure complete precipitation. The solid was filtered, washed with methanol (3×, 50 mL, and dried in vacuo to give 9.26 g, 93% of $Ru(H)(Cl)(H_2)_2(PCy_3)_2$.

Synthesis of $RuCl_2(PCy_3)_2(=CH—CH=CMe_2)$.

Method A—alkyne route:

Ru(H)(Cl)(H2)(PCy3)2 (1.00 g, 1.43 mmol) under an inert atmosphere is dissolved in 30 mL of dichloromethane cooled to −30° C., and 3-chloro-3-methyl-1-butyne (170 μL, 1.5 mmol) is added. The solution instantly turns dark red-purple, and is allowed to stir for fifteen minutes before removing the flask from the cooling bath and concentrating to a viscous oil. Degassed methanol (20 mL) is added to precipitate the purple solid, which is then washed with methanol (3×, 10 mL) and dried to give 1.09 g or approximately 95.2% yield of the carbene.

Selected NMR data $(CD_2Cl_2)$: $^1H$:δ 19.26 (d, RuCH, $J_{HH}$=11.7 Hz), 7.81 (d, RuCHCH, $J_{HH}$=11.7 Hz); $^{31}P$:δ 36.4 (s, $RuPCy_3$); $^{13}C$: δ 288.4 (t, $Ru^CH$, $J_{CP}$=9.6 Hz), 146.9 (s), 133.5 (s).

NMR studies show that this reaction at −30° C. is extremely clean (no other carbene species) and proceeds to approximately 99%. At room temperature the reaction is less clean (i.e., other presumed and unidentified carbene species are generated in small quantities) but also proceeds in ~98% yield. Therefore, the use of low temperatures for the generation of this compound should give a slightly easier isolation and higher yield of a pure product. However, the generation of this carbene for use in situ can be done at room temperature with little or no visible effect.

All other reactions with $Ru(H)(Cl)(H_2)(PCy_3)_2$ described in the description portion of the specification were done in a similar fashion but on a 20 mg scale in 0.5 mL of $CD_2Cl_2$. Non commercially available alkynes were made following procedures in *Preparative Acetylenic Chemistry*, L. Brandsma, Elsevier Science Publishers B. V. (Amsterdam, 1988); H. Werner, et al., *Chem. Ber.* 122: 2097–2107 (1989); and K. Hiraki, et al., *J. Chem. Soci.*, Dalton Trans. pp.873–877 (1985), all of which are incorporated herein by reference.

Method B—triarylphosphine version of the alkyne route 0.24 mL of 3-chloro-3-methyl-1-butyne was added to a −30° C. solution of $Ru(H)(Cl)(PPh_3)_3$ (2.0 g, 1.99 mmoles) in methylene chloride (20 ml). The reaction mixture was stirred for 1.5 hour at 0° C. After the volume was reduced to 1 mL under reduced pressure, 20 mL of pentane was added. The resulting brown solid was isolated by filtration, redissolved in 1 mL of methylene chloride and then was washed twice with 10 mL portions of pentane to yield 1.5 grams (90% yield) of the desired product.

Method C—in situ generation of $Ru(H)(Cl)(H_2)(PCy_3)_2$ $[RuCl_2(COD)]_x$ (0.500 g, 1.78 mmol) and tricyclohexylphosphine (1.050 g, 3.75 mmol) were placed in a 250 mL thick walled teflon-valved Strauss flask. To this system, 20 mL of degassed sec-butanol is added. The system is then placed under vacuum, purged with hydrogen, sealed, and heated to 80° C. After four hours the system is cooled to room temperature, re-pressurized with hydrogen, and allowed to stir at 80° C. for a further sixteen hours. The system is then cooled to room temperature and one volume of toluene is added. The resulting solution is cooled to −30° C. and 2-methyl-1-buten-3-yne (254 mL, 2.66 mmol) is added. After stirring for one hour the solution is concentrated by half and 50 mL of degassed methanol is added to give a purple solid, isolated as above to give 0.590 g, 41% of $RuCl_2(PCy_3)_2(=CH—CH=CMe_2)$.

Synthesis of $RuCl_2(PCy_3)_2(=CH—CH=CMe_2)$—one pot method.

$[RuCl_2(COD)]_x$ (0.500 g, 1.79 mmol) and tricyclohexylphosphine (1.000 g, 3.58 mmol) were placed in a 500 mL high pressure system equipped with a pressure gauge. To this system, 25 mL of degassed sec-butanol and triethylamine (0.250 mL, 1.79 mmol) were added. After purging with hydrogen, the system was pressurized with 1.5 atm of hydrogen and heated to 80° C. for a total of 20 hours, repressurizing as needed. An orange precipitate, known to be $Ru(H)(H_2)_2Cl(PCy_3)_2$ is observed as well as a slightly brown solution. The apparatus was then cooled to room temperature, and then to 0° C., at which point it was purged with argon. 3-chloro-3-methyl-1-butyne (0.600 mL, 5.3 mmol) is added. Over a period of one hour the orange precipitate turns red-purple, and the reaction is then removed from the ice bath and allowed to stir for one additional hour. Degassed methanol (25 mL) is added to precipitate the purple solid, which is then washed with methanol (3×10 mL) and dried to give 1.35 g, 94.5% of the carbene. Selected NMR data $(CD_2Cl_2)$:$^1H$:d19.26 (d, RuCH, $J_{HH}$=11.7 Hz, 1H), 7.81 (d, RuCHCH, $J_{HH}$=11.7 Hz, 1H); $^{31}P$:d 36.4 (s, RuPCy3); $^{13}C$: d 288.4 (t, RuCH, $J_{CP}$=9.6 Hz), 146.9 (s), 133.5 (s).

Synthesis of $RuCl_2(P^iPr_3)_2Cl_2Ru(=CH—CH=CMe_2)$—one pot method.

This procedure is identical to the one pot method for the synthesis of $RuCl_2(PCy_3)_2(=CH—CH=CMe_2)$ except that triisopropyl phosphine (0.573 g, 3.58 mmol) is used instead of tricyclohexylphosphine. In this case the intermediate Ru(H)(H$_2$)$_2$Cl(PiPr$_3$)$_2$ is soluble, giving a red-brown solution which is then cooled and to which the 3-chloro-3-methyl-1-butyne is added. The reaction is quite vigorous, with gas evolved immediately and a deep purple precipitate observed. After stirring for thirty minutes the solid is isolated as above to give 1.85 g, 92.5% of the carbene. Selected NMR data (CD$_2$Cl$_2$):$^1$H:d19.38 (d, RuCH, J$_{HH}$=11 Hz, 1H), 7.95 (d, RuCHCH, J$_{HH}$=11 Hz, 1H), 2.80 (m, PCH(CH$_3$)$_2$, 6H), 1.54 and 1.26 (s, RuCHCHC(CH$_3$)$_2$, 3H each), 1.23 (dd, P PCH(CH$_3$)$_2$, 36H); $^{31}$P:d 45.8 (s, RuPCy3).

Synthesis of Poly-dicyclopentadiene using in situ generated catalyst.

The in situ generation of Ru$_2$Cl$_2$(PCy$_3$)$_2$(=CH—CH=CMe$_2$) (hereinafter referred to as the ruthenium carbene catalyst in this example) is accomplished by dissolving 18 mg (0.025 mmol) of Ru(H)(Cl)(H$_2$)$_2$(PCy$_3$)$_2$ in approximately 0.5–1.0 mL of dichloromethane under argon. This solution is cooled to –30° C., at which point 3-chloro-3-methyl-1-butyne (3.5 mL, 0.030 mmol) is added. The solution instantly turns red-purple, and is allowed to stir for fifteen minutes before removing the solvent to give a dark oil. If a solid is desired, the solution can be concentrated and a small amount (<1 mL) of degassed methanol can be added to give a purple solid, which is dried in vacuo (without filtration).

Polymerizations are done by placing the solution obtained below in a 40° C. oil bath for one hour, and then at least one hour in an oven at 100° C.

Method A:

The in situ generated ruthenium carbene catalyst is dissolved in 25 mL of DCPD and poured into a beaker.

Method B:

The in situ generated ruthenium carbene catalyst is dissolved in 5 mL of DCPD which contains 40 mg of triphenylphosphine, and allowed to stir under argon. After four hours the solution has become quite viscous and is added to 20 mL of DCPD in a beaker.

Method C:

The in situ generated ruthenium carbene catalyst is dissolved in 1 mL of DCPD which contains 40 mg of triphenylphosphine, and allowed to stir under argon. After 17 hours this solution has a slimy, soft gelatin like consistency, which can be dissolved in 4 mL of DCPD before being added to 20 mL DCPD in a beaker.

Ru(COD)(COT)+2 PCy$_3$+α,α-dichlorotoluene.

To a solution of Ru(COD)(COT) (0.11 g; 0.33 mmol) and PCy$_3$ (0.19 g; 0.67 mmol) in 15 mL of toluene was added α,α-dichlorotoluene (50 mL; 0.39 mmol). The reaction mixture was stirred at room temperature for two days. The resulting deep brown solution was evaporated, and the residue was washed with acetone and methanol (twice with 5 mL portions) affording the isolation of a purple solid. The NMR spectra of this product were identical to the compound Ru(=CHPh)Cl$_2$(PCy$_3$)$_2$. Yield: 50%.

Ru(H)$_2$(H$_2$)(PCy$_3$)$_2$+styrene+Cl$_2$CHCO$_2$Me.

Styrene (5 mL) was added to a suspension of Ru(H)$_2$(H$_2$)(PCy$_3$)$_2$ (3.0 g, 4.50 mmol) in pentane (50 mL). The red solution immediately obtained was stirred for 1 hour, and Cl$_2$CHCO$_2$Me (0.9 mL, 8.7 mmol) was then added. The reaction mixture was stirred for 45 minutes. The solvent was removed, and the residue was washed with acetone and methanol (twice with 20 mL portions). A purple solid (2.0 g, 54% yield) was isolated whose NMR data were identical to those of RuCl$_2$(PCy$_3$)$_2$(=CHPH).

What is claimed is:

1. A method for synthesizing a compound of the formula Ru(X)$_2$(L)$_2$(=CHR$^1$) comprising:

reacting R$^1$CHX$_2$ with Ru(COD)(COT) in the presence of L in a solvent wherein:

R$^1$ is selected from a group consisting of hydrogen, unsubstituted C$_1$–C$_{20}$ alkyl, substituted C$_1$–C$_{20}$ alkyl, unsubstituted C$_2$–C$_{20}$ alkenyl, substituted C$_2$–C$_{20}$ alkenyl, unsubstituted aryl, and substituted aryl;

X is a halogen; and,

L is a phosphine of the formula PR$^3$R$^4$R$^5$, where R$^3$ is a secondary alkyl or cycloalkyl group, and R$^4$ and R$^5$ are independently selected from aryl, C$_1$–C$_{10}$ primary alkyl, secondary alkyl, or cycloalkyl groups.

2. The method according to claim 1 wherein the R$^1$ includes a functional group selected from a group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

3. The method according to claim 1 wherein

X is chloride;

L is selected from a group consisting of P(cyclohexyl)$_3$, P(cyclopentyl)$_3$, and P(isopropyl)$_3$; and, the solvent is toluene.

4. The method according to claim 1 wherein R$^1$ is phenyl.

5. A method for synthesizing a compound of the formula

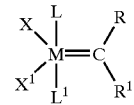

comprising the step of contacting a compound of the formula

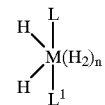

with a compound of the formula RR$^1$C(X)(X$^1$) in the presence of an olefin, wherein n is 1 or 2;

M is osmium or ruthenium;

R and R$^1$ are each independently selected from the group consisting of hydrogen, a substituted substituent, and an unsubstituted substituent, wherein the substituent is selected from the group consisting of C$_2$–C$_{20}$ alkynyl, C$_2$–C$_{20}$ alkyl, aryl, C$_1$–C$_{20}$ carboxylate, C$_1$–C$_{20}$ alkoxy, C$_2$–C$_{20}$ alkoxy, C$_2$–C$_{20}$ alkoxycarbonyl, C$_1$–C$_{20}$ alkylthio, C$_1$–C$_{20}$ alkylsulfonyl or C$_1$–C$_{20}$ alkylsulfinyl;

X and X$^1$ are independently selected from any anionic ligand; and

L and L$^1$ are independently selected from any neutral electron donor.

6. The method according to claim 5 wherein M is ruthenium.

7. The method according to claim 5 wherein R and R$^1$ are each independently selected from the group consisting of hydrogen, unsubstituted C$_1$–C$_{20}$ alkyl, substituted C$_{1-C10}$ alkyl, unsubstituted C$_2$–C$_{20}$ alkenyl, subsituted C$_2$–C$_{20}$ alkenyl, unsubstituted aryl, and substituted aryl.

8. The method according to claim 5 wherein the R or $R^1$ substituent substitution is selected from a group consisting of unsubstituted $C_1$–$C_5$ alkyl, substituted $C_1$–$C_5$ alkyl, unsubstituted $C_1$–$C_5$ alkoxy, substituted $C_1$–$C_5$ alkoxy, unsubstituted aryl, and substituted aryl.

9. The method according to claim 5 wherein $R^1$ includes a functional group selected from a group consisting of hydroxyl, thiol thioether, ketone, aldehyde, ester, ether, amine, imine, amide, amide, nitro, carboxylic acid, disulfide, carbonate, isocyanate, carbodiimide, carboalkoxy, carbamate, and halogen.

10. The method according to claim 5 wherein $R^1$ is phenyl.

11. The method according to claim 5 wherein X and $X^1$ are independently selected from the group consisting of hydrogen, halogen, halogen, a substituted substituent, and an unsubstituted substituent, wherein the substituent is selected from a group consisting of $C_{1-C20}$ alkyl, aryl, $C_1$–$C_{20}$ alkoxide, $C_3$–$C_{20}$ alkyldiketonate, $C_1$–$C_{20}$ carboxylate, aryl or $C_1$–$C_{20}$ alkylsulfonate, $C_1$–$C_{20}$ alkylsulfonyl, and $C_1$–$C_{20}$ alkylsulfinyl.

12. The method according to claim 11 wherein the X or $X^1$ substituent substitution is selected from the group consisting of halogen $C_1$–$C_5$ alkyl, $C_1$–$C_5$ alkoxy, and a phenyl.

13. The method according to claim 11 wherein X and $X^1$ are independently selected from the group consisting of chloride, $CF_3CO_2$, $CH_3CO_2$, $CFH_2CO_2$, $(CH_3)_3CO$, $(CF_3)_2(CH_3)_2CO$, $(CF_3)(CH_3)_2CO$, PhO, MeO, EtO, tosylate, mesylate, and trifluoromethanesulfonate.

14. The method according to claim 5 wherein X and X' are both chloride.

15. The method according to claim 5 wherein L and L' are each independently a phosphine of the formula $PR^3R^4R^5$ wherein $R^3$ is a secondary alkyl or cycloalkyl group and $R^4$ and $R^5$ are each independently selected from a group consisting of aryl, $C_1$–$C_{10}$ primary alkyl, secondary alkyl and cycloakyl groups.

16. The method according to claim 15 wherein L and L' are each independently selected from a group consisting of -P(cyclohexyl)$_3$, -P(cyclopentyl)$_3$, and -P(isopropyl)$_3$.

17. The method according to claim 5 wherein the olefin is a cyclohexene.

18. A method for synthesis a compound of the formula

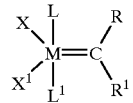

comprising the step of contacting a compound

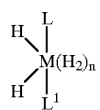

with a compound of the formula $RR^1C(X)(X)$ in the presence of an olefin, wherein n is 1 or 2;

M is ruthenium;

R and $R^1$ are each independently selected from the group consisting of hydrogen, unsubstituted $C_1$–$C_{20}$ alkyl, substituted $C_1$–$C_{20}$, unsubstituted $C_2$–$C_{20}$ alkenyl, substituted $C_2$–$C_{20}$ alkenyl, unsubstituted aryl, and substituted aryl;

X and $X_1$ are independently selected from the group consisting of chloride, $CF_3CO_2$, $CH_3CO_2$, $CFH_2CO_2$, $(CH_3)_3CO$, $(CF_3)_2(CH_3)_2CO$, PhO, MeO, EtO, tosylate, mesylate, and trifluoromethanesulfonate; and L and L' are each independently selected from a group consisting of -P(cyclohexyl)$_3$, -P(cyclopentyl)$_3$, and -P(isopropyl)$_3$.

19. A method for synthesizing a compound of the formula

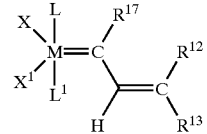

comprising the steps of:

(a) reacting $[M(X^1)_2(R^{20})]_m$ with L and $L^1$ in the presence of $h_2$ to form a reaction mixture; and (b) adding to the reaction mixture a compound of the formula

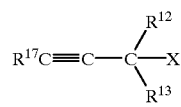

wherein:

m is an integer;

M is osmium or ruthenium;

$R^{12}$ and $R^{13}$ are each independently selected from the group consisting of hydrogen, a substituted substituent, and an unsubstituted substituent, wherein the substituent is selected from the group consisting of $C_2$–$C_{18}$ alkenyl, $C_2$–$C_{18}$ alkyl, aryl, $C_1$–$C_{18}$ carboxylate, $C_1$–$C_{18}$ alkylsulfinyl;

$R^{17}$ is selected from a group consisting of hydrogen, aryl, and $C_1$–$C_{18}$ alkyl;

X and $X^1$ are independently selected from any aniomic ligand;

L and $L^1$ are independently selected from any neutral electron donor; and $R^{20}$ is an olefin.

20. The method of claim 19, wherein M is ruthenium.

21. The method of claim 19, wherein $R^{12}$ and $R^{13}$ are each independently selected from a group consisting of hydrogen, unsubstituted $C_1$–$C_{18}$ alkyl, substituted $C_1$–$C_{18}$ alkyl, unsubstituted $C_2$–$C_{18}$ alkenyl, substituted $C_2$–$C_{18}$ alkenyl, unsubstituted aryl, and substituted aryl.

22. The method of claim 19, wherein the $R^{12}$ or $R^{13}$ substituent substitution is selected from a group consisting of unsubstituted $C_1$–$C_5$ alkyl, substituted $C_1$–$C_5$ alkyl, unsubstituted $C_1$–$C_5$ alkoxy, substituted $C_1$–$C_5$ alkoxy, unsubstituted aryl, and substituted aryl.

23. The method according to claim 19, wherein $R^{12}$ or $R^{13}$ includes a functional group selected from a group consisting of hydroxyl, thiol, thioether, ketone, aldehyde, ester, ether, amine, imine, amide, nitro, carboxylic acid disulfide, carbonate, isocyanate, carbodiimide, carboalkoxy, carbamate, and halogen.

24. The method according to claim 19, wherein $R^{12}$ and $R^{13}$ are both phenyl.

25. The method according to claim 19, wherein $R^{12}$ and $R^{13}$ are both methyl.

26. The method according to claim 19, wherein X and $X^1$ are independently selected from a group consisting of hydrogen, halogen, a substituted substituent, and an unsubstituted substituent, wherein the substituent is selected from a group consisting of $C_2$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, aryl or $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl.

27. The method according to claim 26, wherein the X or $X^1$ substituent substitution is selected from a group consisting of halogen, $C_1$–$C_5$ alkyl, $C_1$–$C_5$ alkoxy, and a phenyl.

28. The method according to claim 19, wherein X and X' are independently selected from the group consisting of chloride, $CF_3CO_2$, $CH_3CO_2$, $CFH_2CO_2$, $(CH_3)_3CO$, $(CF_3)_2(CH_3)_2CO$, $(CF_3)(CH_3)_2CO$, PhO, MeO, EtO, tosylate, mesylate, and trifluoromethanesulfonate.

29. The method according to claim 19, wherein X and $X^1$ are both chloride.

30. The method according to claim 19, wherein L and $L^1$ are each independently a phosphine of the formula $PR^3R^4R^5$ wherein $R^3$ is a secondary alkyl or cycloalkyl group and $R^4$ and $R^5$ are each independently selected from the group consisting of aryl, $C^1$–$C^{10}$ primary alkyl, secondary alkyl and cycloalkyl groups.

31. The method according to claim 19, wherein L and $L^1$ are each independently selected from a group consisting of -P(cyclopentyl)$_3$, and -P(isopropyl)$_3$.

32. Te method according to claim 19, wherein the reacting step of (a) occurs in a solvent.

33. The method according to claim 32, wherein the solvent is sec-butanol.

34. The method according to claim 33, wherein the sec-butanol contains triethylamine.

35. The method according to claim 19, wherein the H2 pressure of (a) is about 1.5 atm.

36. The method according to claim 19, further consisting of the step of:

(c) adding methanol to the reaction mixture.

37. The method according to claim 19, wherein $R^{20}$ is cyclooctadiene.

38. The method according to claim 19, wherein $R^{20}$ is an arene.

39. A method for synthesizing a compound of the formula

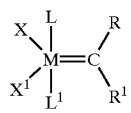

comprising the steps of:

(a) reacting $[MX^2X^3(R^{20})]_m$ with L and $L^1$ in the presence of $H_2$ to form a reaction mixture; and (b) adding to the reaction mixture a compound of the formula $RR^1(X)(X^1)$, wherein:

m is an integer;

M is osmium or ruthenium;

R and $R^1$ are each independently selected from the group consisting of hydrogen, a substituted substituent, and an unsubstituted substituent, wherein the substituent is selected from the group consisting of $C_2$–$C_{18}$ alkenyl, $C_2$–$C_{18}$ alkynyl, $C_{2-C18}$ carboxylate, $C_1$–$C_{18}$ alkoxy, $C_2$–$C_{18}$ alkoxy, $C_2$–$C_{18}$ alkoxycarbonyl, $C_1$–$C_{18}$ alkylthio, $C_1$–$C_{18}$ alkylsulfonyl or $C_1$–$C_{18}$ alkylsulfinyl;

X, $X^1$, $X^2$, and $X^3$ are independently selected from any anionic ligand;

L and $L^1$ are independently selected from any neutral electron donor; and $R^{20}$ is an olefin.

40. The method according to claim 39, wherein (b) further comprises adding an olefin.

41. The method according to claim 39, wherein the olefin is a cyclohexene.

42. The method according to claim 39, wherein the reacting step of (a) occurs in a solvent.

43. The method according to claim 42, wherein the solvent.

44. The method according to claim 43, wherein the sec-butanol contains triethylamine.

45. The method according to claim 39, wherein the H2 pressure (a) is about 1.5 atm.

46. The method according to claim 39, further consisting of the step of:

(c) adding methanol to the reaction mixture.

47. The method according to claim 39, wherein $R^{20}$ is cyclooctadiene.

48. The method according to claim 39, wherein $R^{20}$ is an arene.

* * * * *